United States Patent
Paparatto et al.

(10) Patent No.: US 6,300,506 B1
(45) Date of Patent: Oct. 9, 2001

(54) PROCESS FOR THE PREPARATION OF EPOXITES

(75) Inventors: Giuseppe Paparatto, Cinisello Balsamo; Anna Forlin, Vigonza; Paolo Tegon, Oriago, all of (IT)

(73) Assignee: Enichem S.p.A., San Donato Milanese (IT)

( * ) Notice: Subject to any disclaimer, the term of this patent is extended or adjusted under 35 U.S.C. 154(b) by 0 days.

(21) Appl. No.: 09/626,456

(22) Filed: Jul. 26, 2000

(30) Foreign Application Priority Data

Jul. 27, 1999 (IT) .............................................. MI99A1658

(51) Int. Cl.$^7$ ................................................. C07D 301/12
(52) U.S. Cl. ................................................ 549/531
(58) Field of Search .............................................. 549/531

(56) References Cited

U.S. PATENT DOCUMENTS

| | | | |
|---|---|---|---|
| 5,591,875 | 1/1997 | Chang et al. | |
| 5,859,265 | * 1/1999 | Muller et al. | 549/531 |
| 6,060,610 | * 5/2000 | Arca et al. | 549/531 |
| 6,160,137 | * 12/2000 | Tsuji et al. | 549/523 |
| 6,160,138 | * 12/2000 | Escrig et al. | 549/531 |
| 6,194,591 | * 2/2001 | Grey et al. | 549/533 |
| 6,225,482 | * 5/2001 | Drauz et al. | 549/525 |

FOREIGN PATENT DOCUMENTS

| | | |
|---|---|---|
| 0 712 852 | 5/1996 | (EP) . |
| 0 757 043 | 2/1997 | (EP) . |
| WO 99/48882 | 9/1999 | (WO) . |
| WO 00/17178 | 3/2000 | (WO) . |

OTHER PUBLICATIONS

Database WPI, AN 2000–075359, JP 11–309378, Nov. 9, 1999.

* cited by examiner

*Primary Examiner*—Deborah C. Lambkin
(74) *Attorney, Agent, or Firm*—Oblon, Spivak, McClelland, Maier & Neustadt, P.C.

(57) ABSTRACT

A continuous process is described for the preparation of olefin oxides by direct epoxidation of an olefin with hydrogen peroxide, or compounds capable of producing hydrogen peroxide under the reaction conditions, in a solvent medium, in the presence of a catalytic system consisting of a zeolite containing titanium and a buffer system with a pH controlled within the values of 5.5 to 8.0, consisting of a nitrogenated base and a salt thereof with an organic or inorganic acid. The process allows high conversions and selectivities of the olefin into the corresponding oxide with a catalytic activity stable over a period of time.

25 Claims, No Drawings

PROCESS FOR THE PREPARATION OF EPOXITES

The present invention relates to a continuous process for the preparation of epoxides.

More specifically, the present invention relates to a continuous process for the preparation of propylene oxide by direct epoxidation of propylene with hydrogen peroxide, or compounds capable of producing hydrogen peroxide under the reaction conditions, in a solvent medium, in the presence of a catalytic system consisting of a zeolite containing titanium and a buffer system with a pH controlled within values of 5.5 to 8.0, consisting of a nitrogenated base and a salt thereof with an organic or inorganic acid.

Epoxides, or olefin oxides, are intermediates useful for the preparation of a wide variety of compounds. For example epoxides can be used for the production of glycols, condensation polymers such as polyesters, or for the preparation of intermediates useful in the synthesis of polyurethane foams, elastomers, seals and similar products.

The use of zeolitic compounds with an MFI structure containing titanium atoms (TS-1) as catalysts in the direct epoxidation reactions of olefin compounds with hydrogen peroxide, is known in literature (EP-100,119).

However, the acidity which characterizes these catalysts contributes, together with the possible acidity present in the homogeneous phase, to catalyzing consecutive solvolitic reactions on the epoxide with the opening of the ring. This leads to an increase in production costs for both the decrease in yield to epoxide and for the separation of the by-products formed.

To overcome these disadvantages, processes have been proposed in the art for improving the catalytic performances of these zeolitic compounds by appropriate activation treatment.

For example, the patent EP-230,949 describes an epoxidation process which uses, as catalyst, a titanium silicalite treated, before or during the epoxidation reaction, with a neutralizing agent selected from organic derivatives of silicon of the type $X-Si(R)_3$ or hydrosoluble substances deriving from cations of group I and II with a different base strength.

The patent EP-712,852 relates to an epoxidation process of olefins in the presence of titanium-silicalite which uses as neutralizing agent a non base salt selected from lithium chloride, sodium nitrate, potassium sulfate and ammonium phosphate. Under these conditions the maximum selectivity obtained is in the order of 93%.

The patent U.S. Pat. No. 5,675,026 describes an epoxidation process which uses as catalyst a titanium-silicalite treated, before or during the reaction, with a neutral or acid salt, selected from $Na_2SO_4$, $(NH_4)_2SO_4$, $NH_4NO_3$ or $NaH_2PO_4$.

Operating according to these known processes, propylene oxide is obtained with a good yield and selectivity.

These processes, however, have disadvantages deriving from the fact that these catalytic systems have a short duration of the catalytic cycle and consequently require frequent regeneration.

This creates considerable problems from both a technical and economic point of view, above all when the epoxidation process is carried out in continuous.

In fact, a lowering in the production yield of the epoxide and a reduction in the catalytic activity during the subsequent regeneration phases, have been observed.

It has now been found that it is possible to overcome the disadvantages of the known art described above by means of the process of the present invention, which is based on the use of a buffer system with a pH controlled within the values of 5.5 and 8.0 and which is such that the pH of the reaction system ranges within the above values.

The use of this buffer system has substantial advantages, and in particular:

(i) it allows the catalytic activity to be kept stable over period of time, reducing the frequency of the regeneration cycles of the catalyst to the minimum; and (ii) it allows the preparation of epoxides with high yields and selectivities.

In accordance with this, the present invention relates to a continuous process for the preparation of epoxides by direct oxidation of an olefin with hydrogen peroxide, or compounds capable of producing hydrogen peroxide under the reaction conditions, in a solvent medium, in the presence of a catalytic system consisting of a synthetic zeolite containing titanium atoms and a buffer system with a pH controlled within the values of 5.5 and 8.0, consisting of a nitrogenated base and a salt thereof with an organic or inorganic acid.

The nitrogenated base is selected from compounds having general formula (I)

wherein: R, $R_1$ and $R_2$, the same or different, can be H, an alkyl group with $C_1$–$C_{10}$ carbon atoms, a $-COR_3$ group wherein $R_3$ is an alkyl group with $C_1$–$C_{10}$ carbon atoms or $NH_2$, or a

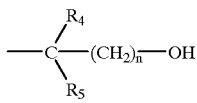

group wherein n is a number from 1 to 10 and $R_4$ and $R_5$ are H or $C_1$–$C_{10}$ alkyl groups.

Preferred compounds having formula (I) are: ammonia, methylamine, ethylamine, diethylamine, trimethylamine, ethanolamine, diethanolamine, triethanolamine, n-proplylamine.

Organic acids which can be used for the purposes of the present invention can be selected from carboxylic acids, such as acetic acid, formic acid, propionic or butyric acid and their derivatives, such as for example oxyacids such as glycol acid and α-lactic acid.

The inorganic acids are selected from sulfuric and phosphoric acid.

Sulfuric acid, acetic acid and formic acid are particularly preferred for the purposes of the present invention.

The olefin compounds which can be used in the process of the present invention can be selected from organic compounds having at least one double bond and can be linear or branched aliphatic, aromatic, alkylaromatic and cyclic. They are preferably olefin hydrocarbons having from 2 to 30 carbon atoms in the molecule and containing at least one double bond.

Examples of olefins suitable for the purposes of the present invention are selected from those having general formula (II)

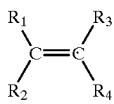

wherein: $R_1$, $R_2$, $R_3$ and $R_4$, the same or different, can be H, an alkyl radical with from 1 to 20 carbon atoms, an aryl radical, an alkylaryl radical with from 7 to 20 carbon atoms, a cycloalkyl radical with from 6 to 10 carbon atoms, an alkylcycloalkyl radical with from 7 to 20 carbon atoms. The radicals $R_1$, $R_2$, $R_3$ and $R_4$, can form, in pairs, saturated or unsaturated rings. These radicals may additionally contain halogen atoms, nitro, nitrile, sulfonic groups and relative esters, carbonyl, hydroxyl, carboxyl, thiol, amine and ether groups.

Examples of olefins which can be epoxidated with the process of the present invention are: ethylene, propylene, allyl chloride, allyl alcohol, butenes, pentenes, hexenes, octeneheptenes-1, 1-tridecene, mesityl oxide, isoprene, cyclo-octane, cyclohexene or bicyclic compounds such as norbornenes, pinenes, etc. The olefins can carry the above substituents both on the unsaturated carbon atoms and on different positions.

The oxidizing agent used in the process of the present invention is hydrogen peroxide ($H_2O_2$) or a compound which is capable of generating $H_2O_2$ under the epoxidation conditions.

An aqueous solution of hydrogen peroxide is preferably used, at a minimum concentration of 1% by weight, preferably with a titer greater than or equal to 35% by weight.

The quantity of hydrogen peroxide with respect to the olefin is not critical, but a molar ratio olefin/$H_2O_2$ ranging from 10:1 to 1:10, preferably from 6:1 to 1:2, is preferably used.

The epoxidation reaction can be carried out in one or more solvents liquid at the epoxidation temperatures. Solvents of a polar nature are typically used, such as alcohols (methanol, ethanol, isopropyl alcohol, t-butyl alcohol, cyclohexanol), hydro-alcohol mixtures, ketones (for example acetone, methyl ethyl ketone, acetophenone), ethers (tetrahydrofuran, butyl ether), aliphatic and aromatic hydrocarbons, halogenated hydrocarbons, esters.

Methanol and, among the ketones, acetone, are preferably used. A mixture of methanol/water with a weight ratio ranging from 50/50 to 99/1, is particularly preferred.

The catalyst which can be used in the process of the present invention is selected from those generally known by the name of titanium-silicalites.

For example titanium-silicalites with an MFI structure can be used, described in the patent U.S. Pat. No. 4,410,501 which also specifies their structural characteristics.

Titanium-silicalites can also be used, in which part of the titanium is substituted by other metals, such as boron, aluminum, iron or gallium. These substituted titanium silicalites and the methods for their preparation are described in European patent applications 226,257, 226,258 and 266,825.

It is also possible to use titanium silicalites with a MEL or intermediate MFI/MEL structure described in Belgian patent 1,001,038. Other titanium-silicalites can be selected from beta zeolites containing titanium and having a BEA structure, described in Spanish patent 2,037,596, ZSM-12 containing titanium and optionally aluminum, described in "Journal of Chemical Communications, 1992, page 745).

The preferred catalyst according to the present invention is titanium-silicalite having the general formula:

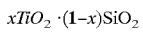

wherein: x represents a number ranging from 0.0001 to 0.04, the value of x preferably ranging from 0.01 to 0.025, and described, for example, in U.S. Pat. Nos. 4,410,501, 4,824,976, 4,666,692, 4,656,016, 4,859,785, 4,937,216.

The quantity of catalyst used in the process of the present invention is not critical; it is selected however in such a way as to allow the epoxidation reaction to be completed in the shortest time possible.

The quantity of catalyst is generally selected in relation to various parameters, such as the reaction temperature, the reactivity and concentration of the olefins, the concentration of hydrogen peroxide, the type and composition of the solvent, the catalytic activity and type of reactor or reaction system used.

The quantity of catalyst typically ranges from 1 to 15% by weight with respect to the reaction mixture, preferably from 4 to 10% by weight.

The catalyst can be used in the form of powder, pellets, microspheres, extruded product or other convenient physical forms.

The temperature used in the process of the present invention generally ranges from 20 to 150° C., preferably from 40 to 100° C. The operating pressure is that which allows the olefin to be maintained in liquid phase at the preset reaction temperature. The operating pressure is generally higher than atmospheric pressure when gaseous olefins are used.

The epoxidation process of the present invention can be carried out in batch, semi-continuous or, preferably, in continuous.

Various types of reactor can be used in the process of the present invention, for example a slurry reactor or a fixed-bed reactor.

The epoxidation process is preferably carried out in continuous, by feeding into a reaction zone containing the catalyst: hydrogen peroxide, the solvent, preferably methanol/water, propylene and an aqueous buffer solution having the composition and pH defined above, so that the pH is controlled in the reactor within values ranging from 5.5 to 8.0, preferably within values ranging from 6 and 7.0.

Conversion refers to the quantity of hydrogen peroxide which reacts during the epoxidation reaction with respect to the quantity charged into the reactor.

Selectivity refers to the number of moles of epoxide produced per moles of reacted hydrogen peroxide.

The epoxidation product obtained with the process of the present invention is separated and recovered from the reaction mixture using conventional techniques such as fractionated distillation.

The following examples have the sole purpose of describing the present invention in greater detail and should in no way be considered as limiting its scope.

Example 1 (Comparative)

Oxidation of Propylene

The epoxidation reaction is carried out in a stirred, 1.5 litre, AISI 316L steel reactor, equipped with a thermostat-regulation system, level control, pressure control and filter for continuously removing the solution, maintaining the catalyst in the reactor.

760 g of a solution of methanol/water (93/7) and 40 g of titanium silicalite TS-1 (EniChem, with a titanium content equal to 2.05% by weight) are initially charged. After thermostat-regulating the system at 50° C. and pressurizing with propylene to 12 bar, the following products are then fed in continuous by means of pumps:

1. 1970 g/hour of a solution of methanol/water 92.8/7.2 by weight
2. 230 g/hour of an aqueous solution of $H_2O_2$ at 35% by weight
3. propylene
4. 100 g/hour of water.

The overall reaction mixture in the feeding (without propylene) is equal to 2300 g/hour and its composition is the following:

$H_2O_2$ 3.5%, $H_2O$ 17%, MeOH 79.5%.

The pressure in the reactor is maintained at 12 bar, feeding propylene.

The reaction trend is followed by taking samples every two hours and determining the residual $H_2O_2$ by titration with sodium thiosulfate and the reaction products by gaschromtography. The pH of the reaction mixture is determined on the liquid effluent leaving the reactor after partially degassing the propylene.

The results are shown in table 1.

TABLE 1

| Time (hrs) | $H_2O_2$ conversion % | PO selectivity % | Reaction pH |
|---|---|---|---|
| 6 | 94 | 65 | 4.5 |
| 16 | 88 | 78 | 4.5 |
| 30 | 85 | 85 | 4.5 |

EXAMPLE 2 (Comparative)

The reaction is carried out under the same conditions as example 1, but using a reaction temperature equal to 60° C. The results are indicated in table 2.

TABLE 2

| Time (hrs) | $H_2O_2$ conversion % | PO selectivity % | Reaction pH |
|---|---|---|---|
| 6 | 90 | 67 | 4.5 |
| 16 | 82 | 75 | 4.5 |
| 30 | 75 | 80 | 4.5 |

EXAMPLE 3

The reaction is carried out as described in example 2, but feeding in continuous (100 g/hour) an aqueous buffer solution containing 0.048% of $NH_3$ and 0.12% of $(NH_4)_2SO_4$ instead of water. The results are shown in table 3.

TABLE 3

| Reaction hours | $H_2O_2$ conversion % | PO selectivity % | Reaction pH |
|---|---|---|---|
| 16 | 97 | 96.8 | 6.1 |
| 30 | 96 | 97.2 | 6.0 |
| 60 | 94 | 97.6 | 6.1 |
| 100 | 94 | 98.1 | 5.9 |

EXAMPLE 4

The same procedure is adopted as in example 2, but feeding (100 g/hour) an aqueous buffer solution containing 0.048% of $NH_3$ and 0.12% of ammonium acetate ($CH_3COONH_4$).

The results are shown in table 4.

TABLE 4

| Reaction Hours | $H_2O_2$ conversion % | PO selectivity % | Reaction pH |
|---|---|---|---|
| 16 | 97 | 96.2 | 6.5 |
| 60 | 95.5 | 97.8 | 6.5 |
| 100 | 94.8 | 98.1 | 6.4 |
| 300 | 95.1 | 98.5 | 6.5 |

EXAMPLE 5

The same procedure is adopted as in example 2, but feeding (100 g/hour) an aqueous buffer solution containing 0.048% of $NH_3$ and 0.10% of ammonium formiate ($HCOONH_4$).

The results are shown in table 5.

TABLE 5

| Time (hours) | $H_2O_2$ conversion % | PO selectivity % | Reaction pH |
|---|---|---|---|
| 16 | 98.0 | 96.2 | 6.4 |
| 60 | 96.2 | 96.8 | 6.3 |
| 100 | 95.2 | 97.2 | 6.3 |
| 400 | 95.1 | 98.0 | 6.3 |
| 600 | 95.0 | 98.1 | 6.3 |

From the data indicated in tables 3, 4 and 5, high conversion and selectivity values are observed together with a stability in the catalyst activity.

EXAMPLE 6 (Comparative)

The same procedure is adopted as in example 2, but feeding (100 g/hour) an aqueous solution containing 0.10% of sodium acetate. The results are shown in table 6.

TABLE 6

| Time (hours) | $H_2O_2$ conversion % | PO selectivity % | Reaction pH |
|---|---|---|---|
| 6 | 96 | 84 | 5.8 |
| 16 | 94 | 91 | 6.0 |
| 30 | 87 | 96 | 6.2 |
| 60 | 75 | 95 | 6.0 |

From the values indicated in the table, a deterioration in the catalyst over a period of time, is observed.

EXAMPLE 7 (Comparative)

The same procedure is adopted as in example 2, but feeding 100 g/hour of an aqueous solution containing 0.10% of $NaNO_3$. The results are shown in table 7.

TABLE 7

| Time (hrs) | $H_2O_2$ conversion % | PO selectivity % | Reaction pH |
|---|---|---|---|
| 6 | 92 | 71 | 4.5 |
| 16 | 87 | 82 | 4.4 |
| 30 | 84 | 86 | 4.5 |

EXAMPLE 8 (Comparative)

The same procedure is adopted as in example 2, but feeding 100 g/hour of an aqueous solution containing 0.04% of NaOH. The results are shown in table 8.

TABLE 8

| Time (hrs) | H$_2$O$_2$ conversion % | PO selectivity % | Reaction pH |
|---|---|---|---|
| 6 | 85 | 93 | 6.6 |
| 16 | 65 | 98 | 7.3 |

EXAMPLE 9 (Comparative)

The same procedure is adopted as in example 2, but feeding 100 g/hour of an aqueous solution containing 0.2% of NaCl. The results are shown in table 9.

TABLE 9

| Time (hrs) | H$_2$O$_2$ conversion % | PO selectivity % | Reaction pH |
|---|---|---|---|
| 6 | 90 | 78 | 4.5 |
| 16 | 85 | 84 | 4.5 |

What is claimed is:

1. A continuous process for the preparation of olefin oxides by the direct epoxidation of an olefin with hydrogen peroxide, or compounds capable of producing hydrogen peroxide under the reaction conditions, in a solvent medium, in the presence of a catalytic system consisting of a zeolite containing titanium atoms and a buffer system with a pH controlled within values ranging from 5.5 to 8.0, consisting of a nitrogenated base and a salt thereof with an organic or inorganic acid.

2. The process according to claim 1, wherein the nitrogenated base is selected from compounds having general formula (I)

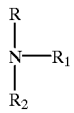
(I)

wherein: R, R$_1$ and R$_2$, the same or different, can be H, an alkyl group with C$_1$–C$_{10}$ carbon atoms, a —COR$_3$ group wherein R$_3$ is an alkyl group with C$_1$–C$_{10}$ carbon atoms or NH$_2$, or a

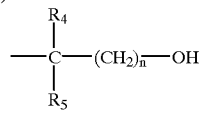

group, wherein n is a number ranging from 1 to 10 and R$_4$ and R$_5$ are H or C$_1$–C$_{10}$ alkyl groups.

3. The process according to claim 2, wherein the nitrogenated base is selected from ammonia, methylamine, ethylamine, dimethylamine, trimethylamine, ethanolamine, diethanolamine, triethanolamine, n-propylamine.

4. The process according to claim 1, wherein the organic acids can be selected from carboxylic acids, such as acetic acid, formic, propionic and butyric acid or their derivatives such as glycolic acid and α-lactic acid.

5. The process according to claim 1, wherein the inorganic acids are selected from sulfuric acid and phosphoric acid.

6. The process according to claim 1, wherein the olefin compounds can be selected from organic compounds having at least one double bond and can be linear or branched aliphatic, aromatic, alkylaromatic and cyclic.

7. The process according to claim 6, wherein the olefin compounds are selected from olefin hydrocarbons having from 2 to 30 carbon atoms in the molecule and containing at least one double bond.

8. The process according to claim 7, wherein the olefin compounds are selected from those having general formula (II)

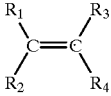

wherein: R$_1$, R$_2$, R$_3$ and R$_4$, the same or different, can be H, an alkyl radical with from 1 to 20 carbon atoms, an aryl radical, an alkylaryl radical with from 7 to 20 carbon atoms, a cycloalkyl radical with from 6 to 10 carbon atoms, an alkylcycloalkyl radical with from 7 to 20 carbon atoms.

9. The process according to claim 8, wherein the radicals R$_1$, R$_2$, R$_3$ and R$_4$ can form, in pairs, saturated or unsaturated rings.

10. The process according to claim 8, wherein the radicals R$_1$, R$_2$, R$_3$ and R$_4$ can contain substituents selected from halogens, nitro, nitrile, sulfonic groups and relative esters, carbonyl, hydroxyl, carboxyl, thiol amine and ether groups.

11. The process according to claim 1, wherein the olefin is propylene.

12. The process according to claim 1, wherein the hydrogen peroxide is used as an aqueous solution with a minimum titer of 1% by weight.

13. The process according to claim 12, wherein the hydrogen peroxide is used as an aqueous solution with a titer equal to or higher than 35% by weight.

14. The process according claim 1, wherein the molar ratio between olefin and hydrogen peroxide ranges from 10/1 to 1/10.

15. The process according claim 14, wherein the molar ratio between olefin and hydrogen peroxide ranges from 6/1 to 1/2.

16. The process according to claim 1, wherein the catalyst is selected from titanium silicalites having general formula (III):

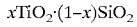

wherein: x ranges from 0.0001 to 0.04.

17. The process according to claim 16, wherein the value of x ranges from 0.01 to 0.025.

18. The process according to claim 16, wherein in the titanium silicalite part of the titanium is substituted by metals selected from boron, aluminum, iron or gallium.

19. The process according to claim 1, wherein the solvent medium is selected from alcohols, hydro-alcohol mixtures, ketones, ethers, aliphatic and aromatic hydrocarbons, halogenated hydrocarbons, esters or glycols.

20. The process according to claim 19, wherein the alcohols are selected from methanol, ethanol, isopropyl alcohol, t-butyl alcohol, cyclohexanol.

21. The process according to claim 20, wherein the ketones are selected from acetone, methyl ethyl ketone, acetophenone.

22. The process according to claim 19, wherein the ethers are selected from tetrahydrofuran and butyl ether.

23. The process according to claim 19, wherein the solvent medium is a mixture of methanol/water with a weight ratio ranging from 50/50 and 99/1.

24. The process according to claim 1, wherein the epoxidation reaction is carried out at a temperature ranging from 20 to 150° C.

25. The process according to claim 24, wherein the temperature ranges from 40 to 100° C.

* * * * *

UNITED STATES PATENT AND TRADEMARK OFFICE
CERTIFICATE OF CORRECTION

PATENT NO. : 6,300,506 B1
DATED : October 9, 2001
INVENTOR(S) : Paparatto et al.

It is certified that error appears in the above-identified patent and that said Letters Patent is hereby corrected as shown below:

<u>Title page, item [54] and Column 1, Line 1,</u>
The title should read:
-- [54] PROCESS FOR THE PREPERATION OF EPOXIDES --

Signed and Sealed this

Thirtieth Day of April, 2002

Attest:

JAMES E. ROGAN
*Attesting Officer*     *Director of the United States Patent and Trademark Office*